(12) United States Patent
Williamson et al.

(10) Patent No.: US 8,299,154 B2
(45) Date of Patent: Oct. 30, 2012

(54) ADHESIVE COMPOSITIONS FOR BONDING COMPOSITES

(75) Inventors: Bobby L. Williamson, Conyers, GA (US); Richard M. Rammon, Stockbridge, GA (US)

(73) Assignee: Georgia-Pacific Chemicals LLC, Atlanta, GA (US)

( * ) Notice: Subject to any disclaimer, the term of this patent is extended or adjusted under 35 U.S.C. 154(b) by 375 days.

(21) Appl. No.: 12/718,391

(22) Filed: Mar. 5, 2010

(65) Prior Publication Data

US 2010/0256289 A1 Oct. 7, 2010

Related U.S. Application Data (60) Provisional application No. 61/158,013, filed on Mar. 6, 2009.

(51) Int. Cl.
C08K 5/00 (2006.01)

(52) U.S. Cl. ......... 524/236; 524/612; 528/405; 528/422

(58) Field of Classification Search ............... 528/405, 528/422; 524/236, 612
See application file for complete search history.

(56) References Cited

U.S. PATENT DOCUMENTS

| | | | |
|---|---|---|---|
| 2,926,154 A | 2/1960 | Keim | |
| 3,494,775 A * | 2/1970 | Coscia et al. | 106/155.1 |
| 4,915,766 A | 4/1990 | Baxter | |
| 6,607,619 B1 | 8/2003 | Foucht et al. | |
| 2007/0054144 A1 | 3/2007 | Dopico et al. | |
| 2010/0285295 A1 * | 11/2010 | Wang et al. | 428/292.4 |

FOREIGN PATENT DOCUMENTS

| | | |
|---|---|---|
| DE | 102007027027 A1 | 12/2008 |
| FR | 2861721 A1 | 5/2003 |
| GB | 1377887 A | 12/1974 |
| JP | 52066600 A | 6/1977 |
| JP | 57057768 A | 4/1982 |
| JP | 05306384 A | 11/1993 |
| JP | 2001354774 A | 12/2001 |
| SU | 896034 A1 | 1/1982 |
| WO | 2006/122749 A1 | 11/2006 |
| WO | 2009/036790 A1 | 3/2009 |

OTHER PUBLICATIONS

International Search Report and Written Opinion of the International Searching Authority for PCT/US2010/026330 mailed May 18, 2010.

* cited by examiner

*Primary Examiner* — Ling Choi
*Assistant Examiner* — Wenwen Cai
(74) *Attorney, Agent, or Firm* — Ram W. Sabnis (57) ABSTRACT

The present invention relates to a non-thermosetting composition made by reacting epichlorohydrin and a primary amine, to the use of that composition for making thermosetting (curable) adhesives suitable for bonding composites, to a method of preparing composites using the thermosetting (curable) adhesives, and to the related composites bonded with the thermosetting (curable) adhesives.

20 Claims, 8 Drawing Sheets

ADHESIVE COMPOSITIONS FOR BONDING COMPOSITES

CROSS-REFERENCE TO RELATED APPLICATION

This application claims the benefit of and incorporates by reference co-pending provisional application Ser. No. 61/158,013 filed Mar. 6, 2009.

FIELD OF THE INVENTION

The present invention is directed to a non-thermosetting composition made by reacting epichlorohydrin and an amine, to the use of that composition for making thermosetting (curable) adhesives, particularly adhesives suitable for bonding composites, to a method of preparing composites, particularly wood composites using the thermosetting (curable) adhesives, and to the related composites bonded with the cured thermosetting (curable) adhesives.

BACKGROUND OF THE INVENTION

A variety of composite materials are made by bonding into a unitary product a primary constituent, often a structural or reinforcement component, using a bonding agent or matrix material, such as an adhesive resin. Composites include engineered wood products (wood-adhesive composite products), insulation products and the like.

Wood-adhesive composite products (i.e., wood composite products), in particular, are used in a wide variety of applications. Regardless of their particular construction, wood composite products (wood composites) often exhibit superior properties to solid wood of similar dimensions. Wood composites are generally stronger, usually exhibit better resistance to degradation and failure, and often are more cost-effective than solid wood alone.

Wood composites, such as plywood, laminated veneer lumber (LVL), oriented strand board (OSB), oriented stand lumber (OSL), waferboard, chipboard, particleboard, flakeboard, medium density fiberboard, hardboard and the like are made by bonding together wood components, be they wood veneers in the case of plywood and LVL, wood strands in the case of OSB and OSL, wood flakes in the case of waferboard, or smaller wood particles in the case of wood composites such as particleboard, etc., using a variety of adhesives, both synthetic adhesives, usually petroleum-based adhesives, and natural adhesives, usually protein-based adhesives.

A feature common to the use of almost all of these adhesives is that the binder, either as a liquid or as a powdered solid, is spread on to or otherwise mixed with the primary constituent (substrate material), for making the composite, such as wood components used to assemble wood composite products. Thereafter, the mixture of the adhesive and the primary constituent of the composite (substrate material) is consolidated into a unitary product, usually using heat to cure the adhesive and often using pressure to increase its density and strength. For example, in the case of wood composite products, the wood components are usually formed into a stack or mat which is then consolidated in a hot platen press to cure the adhesive.

The prior art also has sought ways for accelerating the curing rate and/or enhancing the bonding properties of these adhesives, particularly for making wood composites. For example, U.S. Pat. No. 4,915,766 describes the use of certain acetone-formaldehyde resins as a cure rate accelerating additive for phenol-formaldehyde resins used as an adhesive for wood composites, particularly for making plywood.

More recently, there has been increasing interest in developing ways for reducing formaldehyde emissions associated with the production and use of building materials, including a focus on developing non-formaldehyde based wood adhesives.

US Pub 2007/0054144 describes a non-formaldehyde-based, thermosetting adhesive useful as a wood adhesive. The adhesive comprises a resin having azetidinium functional groups and can be made by reacting an epoxide, such as epichlorohydrin, with a polyamide resin, particularly the reaction product of a dicarboxylic acid, such as adipic acid, and a polyalkylene amine, such as diethylenetriamine. Wood composite products of acceptable properties can be prepared using such azetidinium functional adhesives. Unfortunately, the need to keep the adhesive at a low (acid) pH, usually a pH of about 3-4, to maintain acceptable stability during storage, transportation and use, gives rise to potential corrosion problems with this adhesive.

Indeed, the development of new composites and new techniques for manufacturing such composites that can be used for example in construction applications, particularly those that have the potential for reducing volatile emissions, including formaldehyde emissions, remains a continuing goal of the industry.

The present invention provides a non-formaldehyde containing additive that can be used for formulating non-formaldehyde-based adhesives for manufacturing a wide variety of composites, particularly wood composites.

The non-formaldehyde containing additive also can be used in connection with formaldehyde-based adhesives in a way to reduce formaldehyde emissions without sacrificing the adhesives' ability to produce composites with acceptable properties.

SUMMARY OF THE INVENTION

In one embodiment, the present invention is directed to a non-thermosetting, reaction product of (a) epichlorohydrin and (b) an amine selected from the group consisting of ammonia, a primary amine and mixtures thereof, wherein the reaction product is produced by reacting the epichlorohydrin and the amine in a ratio of 0.25 to 1.0, moles of epichlorohydrin per atom equivalent of amine hydrogen and usually at a ratio of 0.40 to 0.92 moles of epichlorohydrin per atom equivalent of amine hydrogen.

In one embodiment, the present invention is directed to a non-thermosetting, reaction product of (a) epichlorohydrin and (b) an amine selected from the group consisting of ammonia, a primary amine and mixtures thereof, wherein the reaction product is produced by reacting in a serial fashion separate portions of the epichlorohydrin and separate portions of the amine in a ratio of 0.40 to 0.92 moles of epichlorohydrin per atom equivalent of amine hydrogen.

In one embodiment, the present invention is directed to a non-thermosetting, reaction product of (a) epichlorohydrin and (b) an amine selected from the group consisting of ammonia, a primary amine and mixtures thereof, wherein the reaction product is produced by reacting at a temperature of from 30 to 60° C. and in a serial fashion separate portions of the epichlorohydrin and separate portions of the amine in a ratio of 0.40 to 0.92 moles of epichlorohydrin per atom equivalent of amine hydrogen.

In one embodiment, the present invention is directed to a thermosetting adhesive comprising a mixture of (1) a bonding component and (2) a reaction product of (a) epichlorohydrin and (b) an amine selected from the group consisting of ammonia, a primary amine and mixtures thereof, wherein the reaction product is produced by reacting the epichlorohydrin and the amine in a ratio of 0.40 to 0.92 moles of epichlorohydrin per atom equivalent of amine hydrogen.

In other embodiments of thermosetting adhesives according to the present invention, the reaction product is produced by reacting in a serial fashion separate portions of the epichlorohydrin and separate portions of the amine in a ratio of 0.40 to 0.92 moles of epichlorohydrin per atom equivalent of amine hydrogen, wherein the reaction can optionally be conducted at a temperature of from 30 to 60° C.

In one embodiment, the present invention is directed to a method for making a composite comprising (A) applying an adhesive to a substrate material to form a composite precursor and (B) consolidating the composite precursor under heat and optionally under pressure to form the composite, wherein the adhesive comprises a thermosetting mixture of (1) a bonding component and (2) a reaction product of (a) epichlorohydrin and (b) an amine selected from the group consisting of ammonia, a primary amine and mixtures thereof, wherein the reaction product is produced by reacting the epichlorohydrin and the amine in a ratio of 0.25 to 1.0, moles of epichlorohydrin per atom equivalent of amine hydrogen and usually at a ratio of 0.40 to 0.92 moles of epichlorohydrin per atom equivalent of amine hydrogen.

In other embodiments for making a composite according to the present invention, the reaction product that is used in the method is one that is produced by reacting in a serial fashion separate portions of the epichlorohydrin and separate portions of the amine in a ratio of 0.40 to 0.92 moles of epichlorohydrin per atom equivalent of amine hydrogen, wherein the reaction can optionally be conducted at a temperature of from 30 to 60° C.

In one embodiment, the substrate material is a wood component and the mixture of the wood component and the adhesive (the mixture comprising a composite precursor) is consolidated under heat and pressure to form a wood composite.

In one embodiment, the present invention is directed to a composite precursor comprising a combination of (A) a substrate material and (B) an adhesive, wherein the adhesive comprises a thermosetting mixture of (1) a bonding component and (2) a reaction product of (a) epichlorohydrin and (b) an amine selected from the group consisting of ammonia, a primary amine and mixtures thereof, wherein the reaction product is produced by reacting the epichlorohydrin and the amine in a ratio of 0.25 to 1.0, moles of epichlorohydrin per atom equivalent of amine hydrogen and usually at a ratio of 0.40 to 0.92 moles of epichlorohydrin per atom equivalent of amine hydrogen.

In other embodiments of composite precursors according to the present invention, the reaction product is produced by reacting in a serial fashion separate portions of the epichlorohydrin and separate portions of the amine in a ratio of 0.40 to 0.92 moles of epichlorohydrin per atom equivalent of amine hydrogen, wherein the reaction can optionally be conducted at a temperature of from 30 to 60° C.

In one embodiment the composite precursor is a wood composite precursor comprising a combination of a wood component and the adhesive.

In one embodiment, the present invention is directed to a composite comprising (A) substrate material bonded into a unitary structure by (B) a cured adhesive, wherein the adhesive prior to curing comprised a thermosetting mixture of (1) a bonding component and (2) a reaction product of (a) epichlorohydrin and (b) an amine selected from the group consisting of ammonia, a primary amine and mixtures thereof, wherein the reaction product is produced by reacting the epichlorohydrin and the amine in a ratio of 0.25 to 1.0, moles of epichlorohydrin per atom equivalent of amine hydrogen and usually at a ratio of 0.40 to 0.92 moles of epichlorohydrin per atom equivalent of amine hydrogen.

In other embodiments of composites according to the present invention, the reaction product is produced by reacting in a serial fashion separate portions of the epichlorohydrin and separate portions of the amine in a ratio of 0.40 to 0.92 moles of epichlorohydrin per atom equivalent of amine hydrogen, wherein the reaction can optionally be conducted at a temperature of from 30 to 60° C.

In one embodiment the composite is a wood composite and the substrate material is wood components that are bonded into a unitary structure with the cured adhesive.

DETAILED DESCRIPTION OF THE INVENTION

The present invention is directed to an a non-thermosetting, reaction product of (a) epichlorohydrin (hereafter also referred to simply as epi) and (b) an amine selected from the group consisting of ammonia, a primary amine and mixtures thereof, wherein the reaction product is produced by reacting the epichlorohydrin and the amine in a ratio of 0.25 to 1.0, moles of epichlorohydrin per atom equivalent of amine hydrogen and usually at a ratio of 0.40 to 0.92 moles of epichlorohydrin per atom equivalent of amine hydrogen. Alternatively, the reaction product is produced by reacting the epichlorohydrin and the amine in a ratio of 0.40 to 0.60 moles of epichlorohydrin per atom equivalent of amine hydrogen.

Particularly useful non-thermosetting reaction products of (a) epichlorohydrin and (b) an amine selected from the group consisting of ammonia, a primary amine and mixtures thereof are made, as described hereinafter, by reacting in a serial fashion separate portions of the epichlorohydrin and separate portions of the amine in a ratio of 0.40 to 0.92 moles of epichlorohydrin per atom equivalent of amine hydrogen, wherein the reaction can optionally be conducted at a temperature of from 30 to 60° C.

The present invention is particularly directed to using the non-thermosetting reaction product of epi and an amine (hereafter also referred to simply as the epi-amine reaction product) as an additive in thermosetting adhesives for use in preparing composites, particularly wood composites and composites made with fiberous materials such as glass fibers, e.g., insulation-related products. A composition is thermosetting when it has the property of becoming permanently hard and rigid when heated or cured. Thus, thermosetting materials are made of molecules that cross-link with each other after they have been heated, rendering the substance permanently hard and infusible. A non-thermosetting composition, in contrast, is one in which the composition does not become permanently hard and rigid when heated or cured. Thermoplastic compositions are non-thermosetting.

Wood composites that can benefit from the thermosetting adhesives of the present invention in particular, include plywood, laminated veneer lumber (LVL), oriented strand board (OSB), oriented stand lumber (OSL), waferboard, chipboard, particleboard, flakeboard, medium density fiberboard, and hardboard. Thus, in the broad practice of the present invention, the adhesive of the present invention is not limited to manufacture of any particular type of wood composite.

One surprising result that has been observed when using non-thermosetting reaction products of epi and an amine, and particularly ammonia, in preparing wood composites in accordance with the present invention is that the level of formaldehyde emission that is measured from the resulting composites is lower than one would expect simply because of the use of a non-formaldehyde-containing adhesive. This result is demonstrated hereafter in connection with the results of Example 7.

In particular, applicants submit that the epi-amine reaction product of the present invention itself acts as a formaldehyde scavenger and thus exhibits the capability for removing even endogenous formaldehyde associated with wood substrates. As a consequence, use of the epi-amine reaction product of the present invention simply as a formaldehyde scavenger and independent of its crosslinking capability with the bonding products discussed in more detail below also represents an embodiment of the present invention. In this regard, non-thermosetting reaction products of epi and an amine, especially using ammonia as the amine, prepared at the lower ratio of moles of epichlorohydrin per atom equivalent of amine hydrogen would generally be more suitable for formaldehyde scavenging applications.

Formaldehyde emission from composite products, such as particleboard bonded with urea-formaldehyde resins, thus can be controlled in accordance with the present invention by the addition of the epi-amine reaction product of the present invention to the composite product. This can be accomplished in two general ways: (1) one way is to add the epi-amine reaction product of the present invention directly to the adhesive composition used to make the composite product; (2) the second approach involves applying the epi-amine reaction product of the present invention to the, substrate material, e.g., the wood particles themselves, used to form the composite, before applying the adhesive to the substrate.

Ammonia is expected to be the amine of choice for preparing the reaction product of the present invention in most circumstances, due to its general availability, cost and performance. A suitable primary amine for reacting with epi is one having the formula $R1-NH_2$ where R1 is a linear alkyl of 1-4 carbon atoms, a linear hydroxy alkyl of 1-4 carbon atoms, or a linear amino alkyl of 1-4 carbon atoms. Thus, suitable primary amines include methyl amine, ethyl amine, n-propyl amine, ethanolamine, and ethylene diamine. Again, based on availability, cost and performance, ammonia is usually the amine of choice. A combination of the amines also can be used for preparing an epi-amine reaction product.

As understood by those skilled in the art, the value of the atom equivalent of amine hydrogen for any specific amine is easily determined. For example, for ammonia it is determined simply by dividing the number of moles of ammonia ($NH_3$) by three (3). For example, if the amine is ethylene diamine ($H_2N-CH_2CH_2-NH_2$) then the atom equivalent of amine hydrogen is determined simply by dividing the number of moles of ethylene diamine by four (4).

In the broad practice of the present invention, the non-thermosetting, reaction product of the present invention can be prepared by bringing the epi and amine reactant(s) together at the desired ratio of reactants in a suitable reactor and allowing them to react under suitable conditions. As demonstrated in the following examples, the reactants can be combined in a variety of ways to produce a suitable reaction product and in its broadest aspects the present invention is not limited to any particular manner of combining the epi and the amine when synthesizing the epi-amine reaction product. The reaction is usually continued until virtually no unreacted epi remains or no further epi is consumed.

Thus, in accordance with one method, the reaction product of the present invention can be prepared by slowly adding (usually over an extended period of time, for example for a period of about 2-5 hours, depending on the volume of reactants employed) the epi into a full complement of the amine reactant(s) with sufficient mixing in a mutual solvent to ensure a uniform reaction between the epi and the amine(s). The reaction is exothermic so it is advisable to provide cooling at least during the initial, more vigorous portion of reaction between epi and the amine(s). The reaction can then be completed by heating the reaction mixture to an elevated temperature.

Usually, the reaction is conducted in an aqueous solution; as water provides a suitable way for controlling the exothermic reaction. An amount of water sufficient to limit the reactants to not more than 80% of the weight of the reaction mixture, usually between 20% and 80% of the weight of the reaction mixture, often between 30 and 70% of the weight of the reaction mixture and generally between 40 and 65% of the weight of the reaction mixture should be suitable in most instances. Accordingly, the resulting epi-amine reaction product is normally produced as an aqueous mixture containing no more than 80% by weight solids, usually between 20 and 80% by weight solids, often between 30 and 75% by weight solids, and generally between 40 and 65% by weight solids.

The epi-amine reaction conveniently proceeds at a temperature in the range of 20 to 100° C., but is usually conducted at a temperature in the range of 30 to 60° C. In the broadest aspects of the present invention, the epi and the amine are reacted in an amount to provide between 0.25 to 1.0, moles of epichlorohydrin per atom equivalent of amine hydrogen. As noted above, the use of the lower end of this mole ratio range is expected to be especially useful when using the epi-amine reaction product as a formaldehyde scavenger. In other aspects of the present invention, by conducting the reaction using epi and the amine in a ratio of 0.40 to 0.92 moles of epichlorohydrin per atom equivalent of amine hydrogen and alternatively between 0.40 and 0.60 moles of epichlorohydrin per atom equivalent of amine hydrogen usually ensures that virtually all of the amine and the epi are consumed by the reaction and a non-thermosetting reaction product is produced.

In an alternative embodiment, the reactor may contain an aqueous solution of the full complement of epi and the amine then is slowly added to the reactor with sufficient mixing to ensure a uniform reaction between the epi and the amine.

In another embodiment, the reactor may contain a first portion of the amine reactant, preferably as an aqueous solution and then a first portion of the epi is added. The epi can be added slowly as a continuous stream, or as spaced-apart, batch additions. Thereafter, another portion of the amine is added, which again is followed by the addition of another portion of epi. For example, the first portion of the amine may be one-half of the total amount to be used and then one-half of the total amount of epi can be added, for example in 6, 8, 10 or 12 equal, spaced-apart batch portions. Thereafter, the second halves of the amine and epi reactants are added in the same manner. In yet another approach, multiple separate, and alternate additions of amine and epi could be added into a reactor containing water (for example ½, ⅓, ¼, ⅕, ⅙, ⅛, 1/10, 1/12, 1/18, or 1/24 of the total amount of each reactant could be added alternatively over an extended period of time, e.g., over four hours) until the complete amount of both reactants are added into the reactor. In any of these options, the reaction can then be completed by heating the reaction mixture to an elevated temperature in the range of 50 to 100° C., usually not greater than 60° C.

The complete structure of the reaction product has not been determined. The epi-amine reaction product is believed to be populated by molecules that have at least two functional groups selected inter alia from hydroxy, epoxide, azetidinium, alkyl chloride and amino. These functional groups are available for reacting with other moieties, such as secondary amine nitrogens, on the bonding component, or with free formaldehyde (in those cases where the epi-amine reaction product functions as a formaldehyde scavenger). By forming the epi-amine reaction product using a process in which separate portions of the epichlorohydrin and separate portions of the amine are added to a reactor in a serial fashion, applicants believe that the polydispersity of the epi-amine reaction product is increased relative to a process in which the full complement of one of the reactants is in the reactor and then the other reactant is added.

The so-produced aqueous solution of the epi-amine reaction product then can be used directly in its liquid form for making an adhesive or as a formaldehyde scavenger, or the reaction product can be isolated as a particulate solid, for example by spray drying, or by freeze drying before it is used as a component of a thermosetting adhesive or as a formaldehyde scavenger.

In any event, the epi-amine reaction product is then used, in accordance with one embodiment of the present invention, as an additive for preparing an adhesive, such as a thermosetting wood adhesive. To prepare an adhesive, the epi-amine reaction product is blended with a bonding component. An appropriate bonding component is any poly-functional resinous or polymeric material that has a plurality of moieties which are reactive with the functional groups on the epi-amine reaction product. As a result, heating a mixture of a suitable bonding component with the epi-amine reaction product causes cross-linking of the bonding component into a three dimensional cured structure.

Suitable bonding components for use in accordance with the present invention include polyamides, including proteins such as casein, soy and albumin and especially synthetic polyamides such as polyamidoamines, or any mixture thereof; phenol-aldehyde condensate resins, including phenol-formaldehyde (PF) resins, resorcinol-formaldehyde (RF) resins and phenol-resorcinol-formaldehyde (PRF) resins; amine-aldehyde resins, including urea-formaldehyde (UF) resins, melamine-formaldehyde (MF) resins, melamine-urea-formaldehyde (MUF) resins and phenol-melamine-urea-formaldehyde (PMUF) resins and epoxy resins, particularly adducts of bisphenol-A, or novolac resins and epichlorohydrin. Sources of these bonding components, including methods of their production, are well-known and need no further description.

One particularly useful bonding component is a polyamidoamine. Polyamidoamines are well known materials made by reacting a polyamine (e.g., a polyalkylene polyamine such as diethylenetriamine) and a polycarboxylic acid (e.g., a dicarboxylic acid such as adipic or succinic acid) or an ester thereof. Depending on the mole ratio of the polyamine and polycarboxylic acid, the resulting polyamidoamine may retain predominantly primary amine groups or predominantly carboxylic acid groups at the terminal polymer ends. These termini may also have secondary or tertiary amine moieties. Details pertaining to the possible reactants that may be used to prepare polyamidoamines, as well as the reaction conditions and synthesis procedures, are described in U.S. Pat. No. 2,926,154. These materials have long been used in the preparation of paper wet strengthening agents and are well known.

Combining the epi-amine reaction product with a polyamidoamine bonding component produces a non-formaldehyde based, thermosetting adhesive that has bonding properties at least comparable to those achieved using the azetidinium functional adhesives of US Pub 2007/0054144. Indeed, as shown in the Examples that follow, an adhesive of the present invention based on a polyamidoamine bonding component and the epi-amine reaction product has shown improved bonding and lower formaldehyde emissions in the resulting products as compared to a PAE adhesive of the cited publication. Importantly, the epi-amine reaction products of the present invention have a natural pH, i.e., a pH following the synthesis of the epi-amine reaction product, much closer to neutral than the azetidinium functional adhesives of the prior art. As a consequence, the adhesives of the present invention also are able to avoid potential corrosion problems confronting the use of these azetidinium functional adhesives in preparing composites, such as wood composites. In particular, the epi-amine reaction product typically exhibits a pH above about 5, usually between 5 and 7, and often near 6. While the pH can be adjusted, for example by the addition of caustic, to make the pH of the aqueous mixture of the epi-amine reaction product more compatible with a particular bonding product, applicants have determined that the epi-amine reaction product can conveniently and advantageously be used as an aqueous mixture at the natural pH at which it is produced.

The present invention also contemplates using a source of protein as the bonding component for use in preparing a thermosetting adhesive of the present invention. Use of protein in combination with an alternative non-protein bonding component, such as a polyamidoamine, also is contemplated. The protein may be water soluble or water insoluble. The protein may be enzymatically modified, chemically modified or the product of genetic engineering technology. The protein may be substantially pure or may be a part of a mixture such as in a grain fraction. Proteins that may be used to prepare a bonding component therefore include, but are not limited to, grain proteins from grains such as corn, wheat, barley, rice, oat, soya and sorghum, especially soy, and protein fractions obtained from such grains, including gluten and prolamines such as zein, glutenin and gliadin; and animal proteins such as collagen, egg and milk proteins including gelatin, egg albumin (ovalbumin), lactalbumin, casein and sodium caseinate, whey, and milk isolates such as blends of caseinate and whey.

Other suitable classes of bonding components are the low mole ratio phenol-aldehyde resins and amine-aldehyde resins. A low mole ratio phenol-aldehyde and amine-aldehyde resin is a resin where the cumulative mole ratio of the aldehyde reactant, usually formaldehyde, to the phenol or amine reactants is less than 2.5:1, generally is less than 2.0:1, usually is below 1.5:1 and particularly is below 1.3:1. A cumulative mole ratio of the aldehyde reactant, usually formaldehyde, to the phenol or amine reactants is generally within the range of 0.5:1 to 1.5:1 and is usually within the range of 0.8:1 to 1.3:1. A particularly suitable low mole ratio MUF resin is described in U.S. Pat. No. 5,681,917, the disclosure of which is incorporated herein by reference.

To produce a suitable adhesive, the epi-amine reaction product is blended with a bonding component. The epi-amine reaction product is blended with a bonding component in an amount so as to provide a weight ratio of bonding component solids to epi-amine reaction product solids broadly in the range of 99:1 to 1:99, usually in the range of 99:1 to 50:50, more usually at a ratio in the range of 95:5 to 60:40, and often in the range of 95:5 to 70:30. This blending of the epi-amine reaction product and the bonding component is usually done contemporaneously with the preparation of a wood composite as described hereafter.

The thermosetting adhesive of the present invention may further comprise a wax emulsion. Wax emulsions or slack wax are used in producing wood composites having improved moisture resistance or, more specifically, reduced water absorption and water vapor adsorption. For example, suitable wax emulsions are available under the Cascowax brand commercially available from Hexion Specialty Chemicals.

The adhesive of the present invention may also include a variety of other ingredients often added to adhesives destined for use in the preparation of composites, including wood composites. For example, the adhesive may often include a catalyst for enhancing, or accelerating the cure rate of the adhesive. For example, ammonium sulfate is a catalyst often added to enhance the curing of UF and MUF adhesives. The adhesive may also include a formaldehyde scavenger such as back-added urea. However, as noted above, applicants have observed that the epi-amine reaction product itself has shown the capability of scavenging formaldehyde directly. Thus, the epi-amine reaction product has additional utility as an additive for formaldehyde-based adhesives strictly on account of its ability to consume free formaldehyde.

In accordance with the present invention, the adhesive made by blending a bonding component with the epi-amine reaction product and any of the other common ingredients used in such adhesives, is then applied to a substrate material that is used to form the desired composite, such as to the wood component(s) for making a wood composite. As noted above, the substrate material may comprise a fibrous material, such as glass fibers, a wood material usually provided in the form of wood components, or another material used in composite products. The wood component comprises wood layers (e.g., wood veneers), or wood elements, such as wood particles (e.g., sawdust), wood fibers, wood flakes, or wood strands. The wood component(s) may also comprise a mixture of a plant fiber and a wood material. Useful plant fibers include wheat straw fibers, rice fibers, switchgrass fibers, soybean stalk fibers, bagasse fibers, cornstalk fibers, and mixtures thereof. Preferably, in wood composites of the present invention, the wood component is present in the composite in an amount from about 70% to about 98% by weight, on an oven dry basis.

In any event, the adhesive of the present invention may comprise from 0.1 to 99% by weight of the composite, usually comprise from 0.5 to 50% by weight of the composite and often from 1 to 30% by weight of the composite.

Methods of the present invention for making a composite involve applying the adhesive to the substrate material; and then consolidating the so-produced composite precursor material into the ultimate composite by heating often in the presence of some form of molding pressure. For example, the preparation of a wood composite involves applying the thermosetting adhesive to a wood component comprising wood layers, or wood elements, as described above, to yield a wood composite precursor. The thermosetting adhesive may be applied to the wood component in any conventional manner. For example, for a particulate wood component (e.g., wood particles, wood fibers, wood flakes, or wood strands), the wood component may be coated by, sprayed by, mechanically mixed with, etc., a liquid or solid version of the thermosetting adhesive, or the constituents thereof.

Likewise, if wood veneers or layers are used as the wood component, such veneers or layers may be brushed, sprayed, coated, etc., at mating surfaces, with the thermosetting adhesive, prior to consolidation to make a wood composite. Any of the additives of the thermosetting adhesive described above may be combined with the adhesive prior to application to the wood component(s). Alternatively, additives may be introduced separately into the mixture used to prepare the wood composite precursor.

The separate components of the adhesive may be preblended before the adhesive is applied to a substrate, or the separate components of the adhesive may be separately applied to the substrate.

One method of preparing the thermosetting adhesive for subsequent application to the substrate material, such as to wood component, is by continuous mixing of separate liquid streams of a bonding component and the epi-amine reaction product (e.g., cross-linking agent). The flow rates of the streams may be continuously monitored and adjusted to provide a ratio in the thermosetting adhesive of the bonding component solids to the epi-amine reaction product solids that varies in response to one or more measured variables (e.g., wood moisture content). Such a method is described, for example, in U.S. Pat. No. 6,607,619.

Another method involves applying the thermosetting adhesive in a liquid form to a substrate material, such as a wood component (e.g., particulate or layered material), by a nozzle atomizer or by a spinning-disk atomizer. Thermosetting adhesive may also be applied in a powder form by mixing a particulate form of the bonding component with a particulate form of the epi-amine reaction product. In another embodiment, a thermosetting adhesive can applied onto a substrate material, such as a wood component, by first spraying the substrate material (e.g., wood component) with liquid bonding component and thereafter combining the so-sprayed substrate material (e.g., wood component) with a powder form of the epi-amine reaction product. Both liquid and powder forms of the bonding component and epi-amine reaction product constituents of the thermosetting adhesive may be used in combination to reduce the amount of moisture added to any substrate material, often a particularly important consideration in the bonding of certain wood components.

A composite precursor material, such as a wood composite precursor composition, for preparing a composite, such as a wood composite, therefore simply comprises the mixture of a thermosetting adhesive of the present invention and the substrate material, such as a wood component, to which the adhesive is applied in any manner, such as those described above.

In making the wood composite, in particular, the wood composite precursor composition is first formed into substantially the shape of the composite. The shaped composition is then consolidated to provide the composite. The wood composite precursor is typically consolidated, for example, by applying heat, often in concert with the application of pressure, to form a wood composite having desired dimensions (e.g., thickness). By consolidating the composition of the present invention, wood composite products exhibiting excellent strength characteristics and a reduced level of volatile emissions (especially formaldehyde) can be produced. For example, wood composite products of the present invention can be produced having internal bond (IB) strengths, modulus of ruptures (MORs), and modulus of elasticity (MOEs) sufficient to satisfy industry standards as measured according to ASTM D 1037, see American National Standards Institute (ANSI) A-208-1 in particular for particleboard testing.

Regardless of the technique used to apply the adhesive to the wood component, the adhesive-treated wood material (wood composite precursor) is formed into a mat and positioned within a press cavity for consolidating the mat into a unitary composite. Such presses generally have a press cavity defined by opposing press platens. The press platens are heated and the press may also be designed to allow steam to be injected into the cavity where the wood composite is formed between the platens.

As is recognized in the art, for any given adhesive, the resulting bond strength often can be increased or decreased by increasing or decreasing the amount of adhesive applied, relative to the amount of substrate material, such as a wood component. The amount of curable, adhesive used for manufacturing a composite, such as a wood composite panel, will generally depend on the characteristics desired in the final composite product. Generally, for a wood composite the amount of adhesive can vary from about 1 weight percent up to about 40 weight percent of adhesive solids based on oven dry weight of the substrate material, such as a wood component. Usually, at least 2 percent by weight and no more than about 30 percent by weight should be needed in most cases. While more adhesive solids than 30 weight percent can be used; a greater amount is not usually cost efficient. Thus, adequate bond strengths usually can be obtained by forming and consolidating compositions for preparing wood composites, wherein the wood component usually is present in an amount from 75-95% by weight, on an oven dry basis (alternatively adhesive solids of 5-25% by weight on the basis of the oven dry wood).

In producing particleboard, fiberboard (e.g., medium density fiberboard), waferboard, OSB and the like, in accordance with the present invention, a wood composite precursor composition, containing the adhesive and a particulate wood component, may be formed into substantially the shape of a mat (e.g., by spreading the precursor composition onto a flat surface). The mat may then be consolidated or cured under heat and pressure to form the particleboard or fiberboard wood composite. Procedures for forming mats are known in the art and are described, for example, by Maloney, MODERN PARTICLEBOARD AND DRY-PROCESS FIBERBOARD MANUFACTURING, Miller Freeman Publications, San Francisco, Calif. (1997). The formed mat is pressed to a pre-determined thickness at a sufficient pressure and at a temperature preferably ranging from about 150° C. (300° F.) to about 218° C. (425° F.) for a time from about 3 minutes to about 20 minutes, in order to cure the thermosetting adhesive and obtain the wood composite. Preferably, the mat is pressed at about 165° C. (330° F.). The pressure used may be within the range from about 100 psi to about 600 psi, and varies according to the press temperature, particular adhesive, type of wood composite, and other factors recognized by those skilled in the art. In a typical consolidation operation to prepare particleboard, a high pressure (e.g., 600 psi) is applied initially, followed by a steady "bleeding" of the pressure as the thermosetting adhesive cures at the consolidation temperatures described above. Thus, in a normal commercial particleboard manufacturing operation, continuous or multi-opening presses are heated to 165° C. (330° F.) to 180° C. (360° F.) and used to apply pressures of up to about 600 psi. Press or cycle times will typically be within the range given above, but can vary depending on the type of press, press temperature, and board thickness. Advantageously, using the adhesives of the present invention, these conditions are not expected to differ significantly, relative to conventional practices using, for example, urea-formaldehyde based adhesives.

Wood layers or veneers can be used as the wood component described above to produce wood composites. For example, plywood and LVL can be made from a plurality of wood layers or veneers by applying the thermosetting adhesive of the present invention to mating surfaces of these wood layers or veneers and thereafter consolidating them. In the case of plywood, consolidation typically comprises (i) pre-pressing the surface or surfaces of wood veneers, to which the adhesive has been contacted, under pre-pressing conditions to form a panel, followed by (ii) hot-pressing the panel at curing conditions to cure the adhesive. Pre-pressing conditions typically include ambient temperature, a pressure from about 150 psi to about 175 psi, and a time of less than about 10 minutes. The degree of pre-pressing is normally just sufficient to produce panels that resist delamination under normal conditions of storage and handling. After pre-pressing, hot-pressing is conducted to carry out or complete the cure of the thermosetting adhesive. Hot-pressing conditions preferably include a temperature from about 135° C. (275° F.) to about 232° C. (450° F.), a pressure from about 165 psi to about 350 psi, and a time from about 1 minute to about 80 minutes.

While acceptable wood composite products can be obtained using a wood component having an average moisture content above 10 percent by weight, for more efficient operation, the average moisture content of the wood components in the mat entering the press should not exceed about 9 percent by weight. Usually, the average moisture content of the wood component will be between 3 percent and 9 percent by weight.

In accordance with the method of the present invention, once the wood composite precursor is readied for consolidation, a mat is formed in or is introduced into a suitable press cavity. After the wood composite precursor mat is disposed within the press cavity, the press can be closed to its final position for making a wood composite product of a specific thickness. The quantity of wood components introduced into the press is proportioned so that closing the press to the desired thickness for the wood composite can be accomplished at conventional press platen pressures. Consolidation pressures within the mat between about 80 to 750 psig are typical. Typical press platen temperatures can range from about 135° C. to 230° C. (275° F. to 446° F.), with a press platen temperature of about 210° C. (410° F.) being more typical.

In further embodiments, the present invention is:

1. A non-thermosetting, reaction product of (a) epichlorohydrin and (b) an amine selected from the group consisting of ammonia, a primary amine and mixtures thereof, wherein said reaction product is produced by reacting the epichlorohydrin and the amine in a ratio of 0.25 to 1.0, moles of epichlorohydrin per atom equivalent of amine hydrogen and usually at a ratio of 0.40 to 0.92 moles of epichlorohydrin per atom equivalent of amine hydrogen.
2. A thermosetting adhesive comprising a mixture of (1) a bonding component and (2) a reaction product of (a) epichlorohydrin and (b) an amine selected from the group consisting of ammonia, a primary amine and mixtures thereof, wherein said reaction product is produced by reacting the epichlorohydrin and the amine in a ratio of 0.25 to 1.0, moles of epichlorohydrin per atom equivalent of amine hydrogen and usually at a ratio of 0.40 to 0.92 moles of epichlorohydrin per atom equivalent of amine hydrogen.
3. A method for making a composite comprising (A) applying an adhesive to a substrate material to form a composite precursor and (B) consolidating the composite precursor under heat to form the composite, wherein the adhesive comprises a thermosetting mixture of (1) a bonding component and (2) a reaction product of (a) epichlorohydrin and (b) an amine selected from the group consisting of ammonia, a primary amine and mixtures thereof, wherein said reaction product is produced by reacting the epichlorohydrin and the amine in a ratio of 0.25 to 1.0, moles of epichlorohydrin per atom equivalent of amine hydrogen and usually at a ratio of 0.40 to 0.92 moles of epichlorohydrin per atom equivalent of amine hydrogen.
4. A composite precursor comprising a combination of (A) a substrate material and (B) an adhesive, wherein the adhesive comprises a thermosetting mixture of (1) a bonding component and (2) a reaction product of (a) epichlorohydrin and (b) an amine selected from the group consisting of ammonia, a primary amine and mixtures thereof, wherein said reaction product is produced by reacting the epichlorohydrin and the amine in a ratio of 0.25 to 1.0, moles of epichlorohydrin per atom equivalent of amine hydrogen and usually at a ratio of 0.40 to 0.92 moles of epichlorohydrin per atom equivalent of amine hydrogen.
5. A composite comprising (A) substrate material bonded into a unitary structure by (B) a cured adhesive, wherein the adhesive prior to curing comprised a thermosetting mixture of (1) a bonding component and (2) a reaction product of (a) epichlorohydrin and (b) an amine selected from the group consisting of ammonia, a primary amine and mixtures thereof, wherein said reaction product is produced by reacting the epichlorohydrin and the amine in a ratio of 0.25 to 1.0, moles of epichlorohydrin per atom equivalent of amine hydrogen and usually at a ratio of 0.40 to 0.92 moles of epichlorohydrin per atom equivalent of amine hydrogen.
6. Any of the previous embodiments or any of the subsequent embodiments wherein the epi-amine reaction product is produced by reacting in a serial fashion separate portions of the epichlorohydrin and separate portions of the amine.
7. Any of the previous embodiments or any of the subsequent embodiments wherein the epi-amine reaction product is produced by reacting in a serial fashion and at a temperature of from 30 to 60° C. separate portions of the epichlorohydrin and separate portions of the amine.
8. Any of the previous embodiments or any of the subsequent embodiments wherein the epi-amine reaction product is produced by reacting in a serial fashion separate portions of the epichlorohydrin and separate portions of the amine at a temperature of not greater than 60° C.
9. Any of the previous embodiments, or any of the subsequent embodiments wherein the epi-amine reaction product is produced by reacting the epichlorohydrin and the amine in a ratio of 0.40 to 0.60 moles of epichlorohydrin per atom equivalent of amine hydrogen.
10. Any of the previous embodiments, or any of the subsequent embodiments wherein the amine is selected from the group consisting of ammonia, a primary amine and mixtures thereof, wherein the primary amine has a formula $R1-NH_2$ where R1 is a linear alkyl of 1-4 carbon atoms, a linear hydroxy alkyl of 1-4 carbon atoms, or a linear amino alkyl of 1-4 carbon atoms.
11. Any of the previous embodiments, or any of the subsequent embodiments wherein the amine is selected from the group consisting of ammonia, methylamine, ethylamine, n-propyl amine, ethanolamine, ethylenediamine and mixtures thereof.
12. Any of the previous embodiments, or any of the subsequent embodiments wherein the composite is a wood composite and the substrate is a wood component.
13. Any of the previous embodiments wherein the bonding component is selected from the group consisting of polyamides, phenol-aldehyde condensate resins, amine-aldehyde resins and epoxy resins.
14. Any of the previous embodiments, or any of the subsequent embodiments wherein the bonding component is a polyamidoamine.
15. Any of the previous embodiments, or any of the subsequent embodiments wherein the bonding component is a protein.
16. Any of the previous embodiments, or any of the subsequent embodiments wherein the bonding component is soy protein.
17. Any of the previous embodiments, or any of the subsequent embodiments wherein the bonding component is selected from the group consisting of phenol-formaldehyde (PF) resins, resorcinol-formaldehyde (RF) resins and phenol-resorcinol-formaldehyde (PRF) resins.
18. Any of the previous embodiments, or any of the subsequent embodiments wherein the bonding component is selected from the group consisting of urea-formaldehyde (UF) resins, melamine-formaldehyde (MF) resins, melamine-urea-formaldehyde (MUF) resins and phenol-melamine-urea-formaldehyde (PMUF) resins.
19. Any of the previous embodiments wherein the bonding component is a low mole ratio phenol-aldehyde resin, or a low mole ratio amine-aldehyde resin.

The following examples provide illustrative embodiments of the present invention and are not intended as a limitation on the scope of the invention. Unless otherwise indicated, all parts and percentages are by weight. In the following examples, the internal bond (IB), modulus of ruptures (MORs) and modulus of elasticity (MOEs) are measured in accordance with the current version of ASTM D1037, see also American National Standards Institute (ANSI) A-208-1 (2008) in particular for particleboard testing.

EXAMPLE 1

Preparation of an Epi-Ammonia Reaction Product

Water (18.71 parts by weight (pbw)) and ammonia (8.67 pbw of a 30% by weight aqueous solution—ammonium hydroxide) are loaded into a suitable reactor. The temperature of the aqueous mixture is adjusted to 25° C., agitation is initiated and is maintained throughout the remainder of the process. Over periods of 4-6 hours, twelve (12) separate charges of 2.06 pbw of epichlorohydrin (epi) are added into the agitated reactor), e.g., a charge is added about every 20 minutes. An exotherm ensues, which is allowed to raise the temperature of the reaction mixture to about 35 to 40° C. That temperature is maintained throughout the additions. With the temperature adjusted to 35° C., an additional charge of ammonia (12.43 pbw of a 30% by weight aqueous solution—ammonium hydroxide) is added to the reactor, followed by additional additions of epi. In particular, over an additional period of 4-6 hours, twelve (12) additional charges of 2.95 pbw of epichlorohydrin are thereafter added into the agitated reactor, again a charge is added about every 20 minutes. As in the first half of the process, the ensuing exotherm is controlled such that the temperature of the reaction mixture is maintained at about 35 to 40° C. throughout the additions. Once all of the epi has been added, the temperature of the reaction mixture is allowed to increase, with added heat as necessary, over a period of 15 minutes to establish a temperature of 50° C., and the reaction mixture is held at that temperature for 30 minutes. Then, over a period of 10 minutes, the temperature of the reaction mixture is allowed to increase, with added heat as necessary, to a temperature of 60° C., and the reaction mixture is held at that temperature for 4 hours. At that point, the reaction mixture is cooled to 35° C., and the product is then pumped to storage. The total solids of the aqueous epi-ammonia reaction product is expected to be about 66.5% by weight, and the pH about 5.7.

EXAMPLE 2

Epi-Amine Reaction Products Syntheses Comparison

A series of epi-amine reaction products were prepared as follows:

Process 1—with all of the epichlorohydrin and water in the reactor, the addition of the ammonium hydroxide (aqueous ammonia) was programmed to be added slowly over about 3 hours; while allowing the resulting exotherm to heat the reaction mixture to a temperature of about 35° C. and then maintaining the temperature at about 35° C. throughout the remainder of the addition. Following the addition of all the ammonia, the reaction mixture was allowed to exotherm to 50° C., held at that temperature for about 4 hours and then cooled to 25° C. where it was held overnight. The next day the reaction mixture was heated to 60° C., held for one hour and then cooled to 25° C.

Process 2—with all of the water and one-half of the ammonium hydroxide (aqueous ammonia) in the reactor, half of the epichlorohydrin was added in 12 equal portions over a period of about 90-150 minutes. An exotherm caused a rapid increase in temperature early during the addition of epi and the reaction mixture was cooled to and maintained at a temperature of about 35° C. as the first half of the epi was added. Then, the second half of the ammonium hydroxide was added to the reaction mixture and the remaining epi was added, again in 12 equal portions over a similar time period, while maintaining the temperature at about 35° C. The reaction mixture then was heated to 50° C., held at that temperature for about 4 hours and then cooled to 25° C. where it was held overnight. The next day the reaction mixture was heated to 60° C., held for one hour and then cooled to 25° C.

Process 3—with all of the water in the reactor, 24 equally sized portions of the ammonium hydroxide (aqueous ammonia) and 24 equally sized portions of the epichlorohydrin were alternatively added to the reactor over a period of about 4 hours while maintaining the temperature at about 35° C. Following the addition of all the reactants, the reaction mixture was allowed to exotherm to 60° C., held at that temperature for about 4 hours and then cooled to 25° C.

Figure 1:
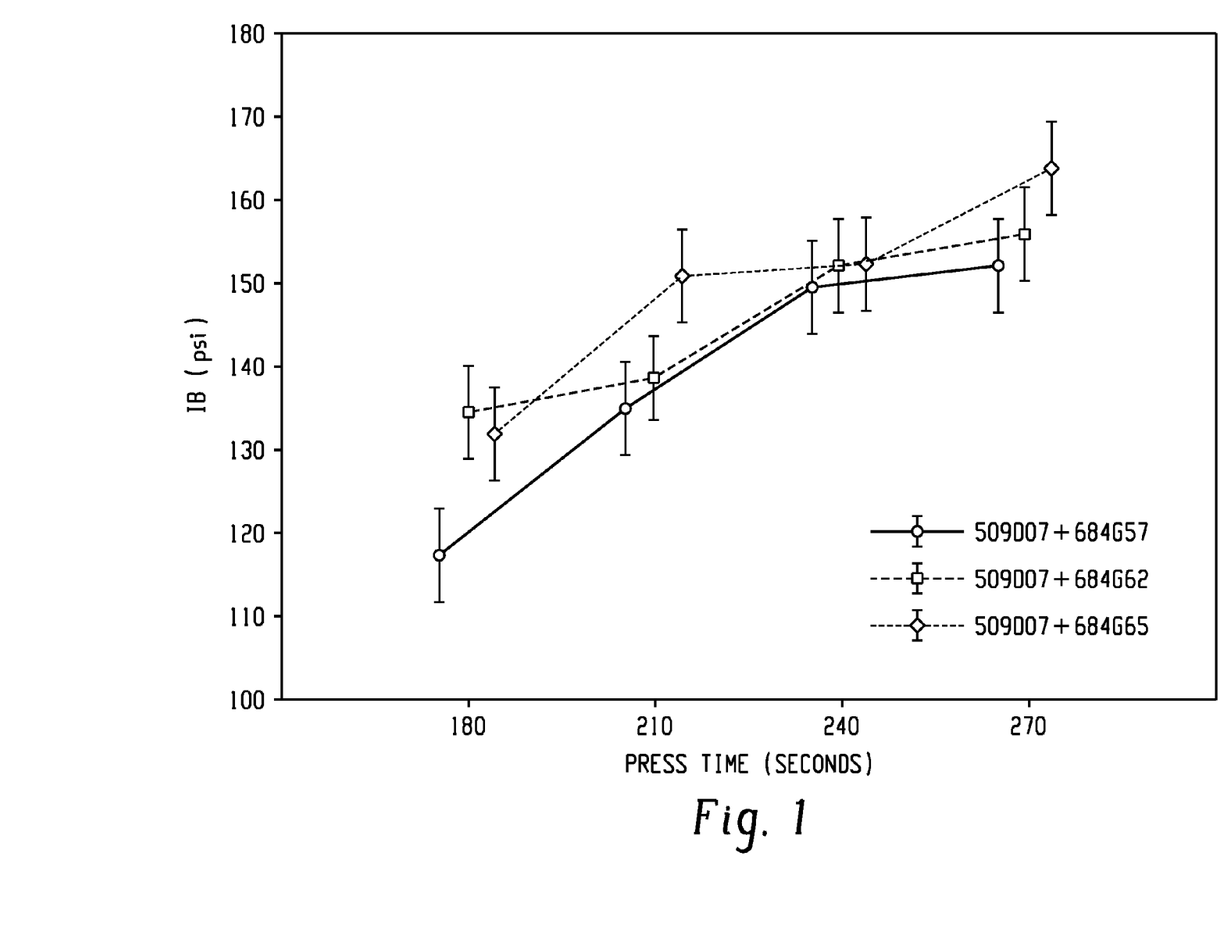
FIG. 1 plots the average internal bond strength (IB) of wood composite panels made at different press times and made using adhesives comprising mixtures of a polyamide bonding component and reaction products of (a) epichlorohydrin and (b) ammonia made according to three different reaction schemes. In this figure and in the following figures, the various data points are placed above the abscissa at the appropriate value in the vicinity of the appropriate X-coordinate so that the statistical bars do not directly overlap and can be viewed individually.
Figure 2:
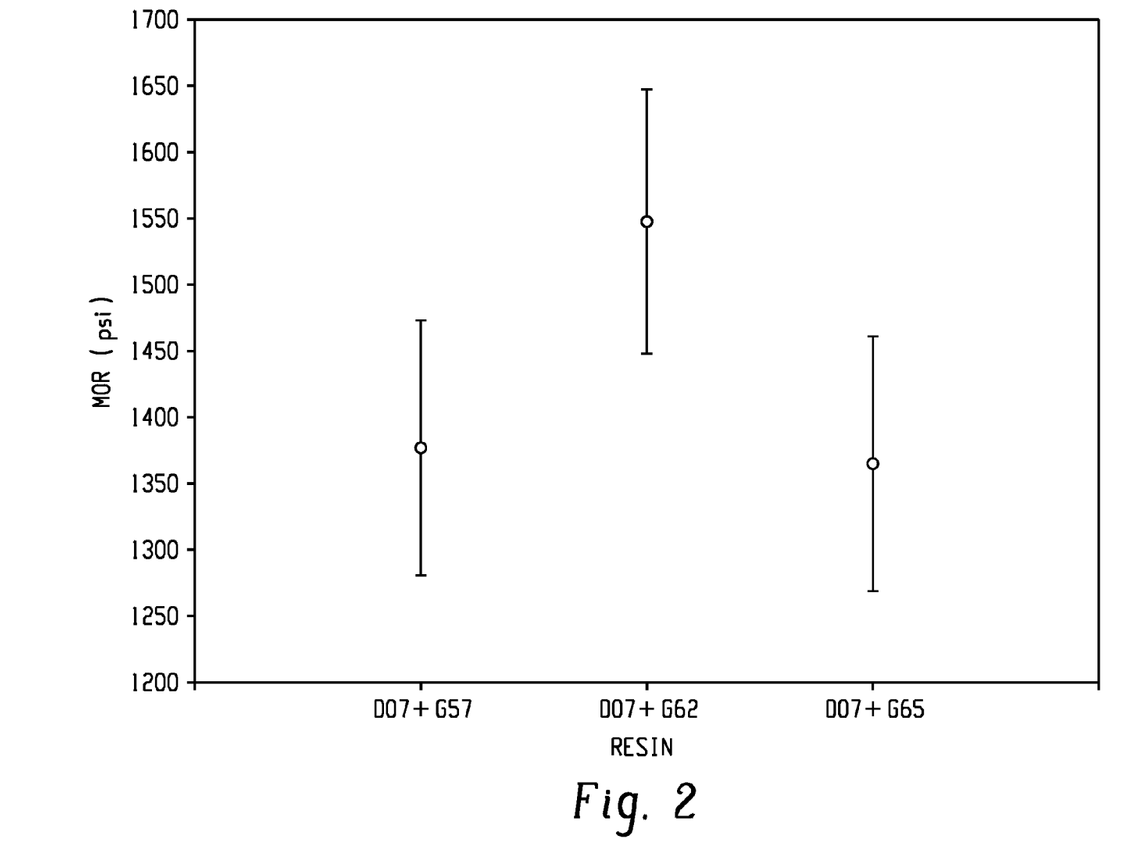
FIG. 2 plots the average Modulus of Rupture (MOR) of wood composite panels made at a 270 second press time and made using adhesives comprising mixtures of a polyamide bonding component and reaction products of (a) epichlorohydrin and (b) ammonia made according to three different reaction schemes.
Figure 3:
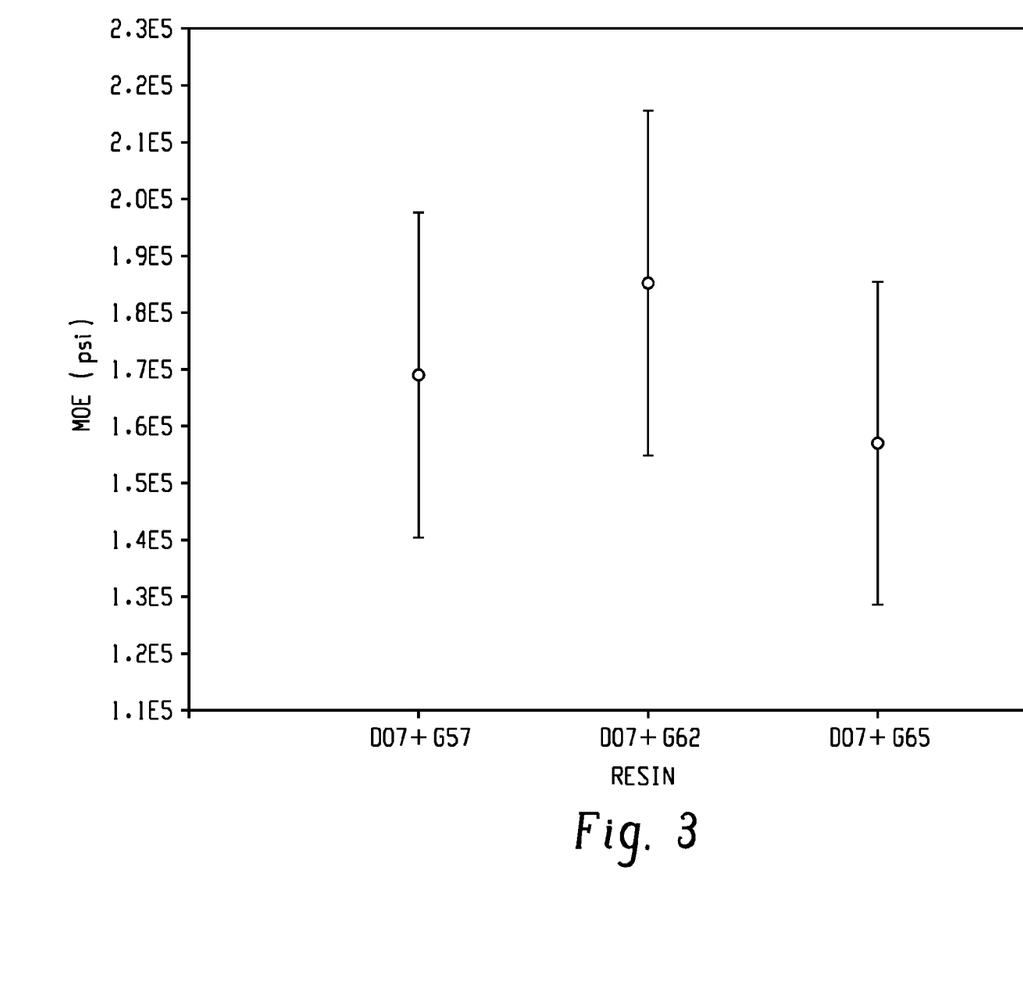
FIG. 3 plots the average Modulus of Elasticity (MOE) of wood composite panels made at a 270 second press time and made using adhesives comprising mixtures of a polyamide bonding component and reaction products of (a) epichlorohydrin and (b) ammonia made according to three different reaction schemes.

The respective epi-amine reaction products obtained in accordance with Process 1, Process 2 and Process 3, and all made at the same epi:ammonia mole ratio, were used to prepare adhesives by blending each of the respective reaction products with the same polyamidoamine polymer in an amount of 75 parts polymer solids and 25 parts reaction product solids. Each of the respective adhesives was used to prepare six (6) ⅝ inch thick panels from the same Southern Yellow Pine wood particles using 8% by weight adhesive solids on the oven dry weight of wood. Four of the panels prepared at press times between 180 and 270 seconds were used for IB testing, and two of the panels prepared at a press time of 270 seconds were used for MOR and MOE testing, respectively. The panels were all pressed at a press temperature of 330° F. (166° C.). All of the panels were prepared at a target density of 45 pounds per cubic foot (7.2 grams per cubic centimeter). The results of the testing are presented in FIGS. 1, 2 and 3.

EXAMPLE 3

Synthesis of Epi-Amine Reaction Products at Various Mole Ratios

A series of epi-amine reaction products were prepared in substantially the same way at various mole ratios of epi to ammonia including 2.77:1, 2.5:1, 2.25:1 and 2.0:1. Table 1 presents data on the amount of residual epi, the amount of byproduct 1,3-dichloro-2-propanol and the viscosity of the respective reaction products.

TABLE 1

| Epi/Ammonia Mole Ratio | % Free Epi[1] | % 1,3-dichloro-2-propanol[1] | Viscosity (cps)[2] |
|---|---|---|---|
| 2.77 | 0.099 | 11.5 | 90 |
| 2.50 | 0.048 | 7.7 | 14 |
| 2.25 | 0.036 | 5.9 | 21 |
| 2.00 | 0.021 | 3.3 | 46 |

[1]Residual Epi and 1,3-dichloro-2-propanol was determined by Gas Chromotograph/Mass Spectrometry (GC/MS)
[2]Brookfield viscosity measured at 25° C. using a Digital Viscometer with a small sample adapter (Model DV-II) at 60-100 rpms.

Figure 4:
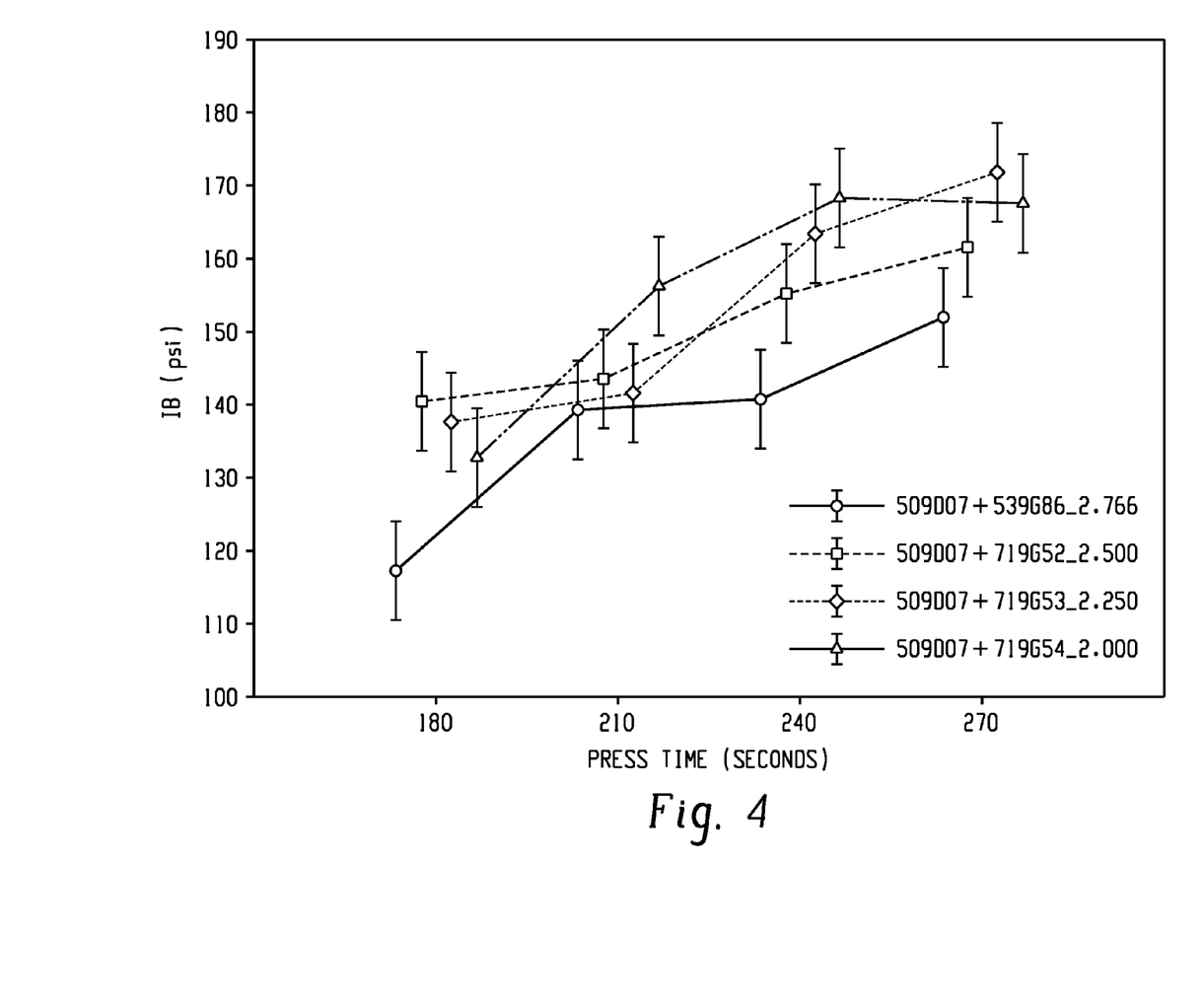
FIG. 4 plots the average internal bond strength (IB) of wood composite panels made at different press times and made using adhesives comprising mixtures of a polyamide bonding component and reaction products of (a) epichlorohydrin and (b) ammonia made at four (4) different mole ratios of epichlorohydrin per atom equivalent of amine hydrogen.

The respective epi-amine reaction products were used to prepare adhesives by blending each of the respective reaction products with the same polyamidoamine polymer in an amount of 66.7 parts polymer solids and 33.3 parts reaction product solids. Each of the respective adhesives was used to prepare six (6) ⅝ inch thick panels from the same Southern Yellow Pine wood particles using 6% by weight adhesive solids on the oven dry weight of wood. Four of the panels prepared at press times between 180 and 270 seconds were used for IB testing, and two of the panels prepared at a press time of 270 seconds were used for MOR and MOE testing, respectively. All of the panels were prepared at a target density of 48 pounds per cubic foot (7.7 grams per cubic centimeter). The panels were all pressed at a press temperature of 330° F. (166° C.). The results of the IB testing are presented in FIG. 4. Any differences among the MOR and MOE results for the boards made with the respective adhesives were not statistically significant.

EXAMPLE 4

Synthesis of Epi-Assorted Amine Reaction Products

A series of epi-amine reaction products were prepared in substantially the same way using a variety of different amines. A comparison or control epi-amine (ammonia) reaction product was prepared at a mole ratio of epi to ammonia of 2.77:1. Then four different epi-amine reaction products were prepared at an epi to amine mole ratio of 2.0:1 using methylamine (MA), ethanolamine (EA), ethylenediamine (EDA) and iso-propylamine (IPA).

The respective epi-amine reaction products were used to prepare adhesives by blending each of the respective reaction products with the same polyamidoamine polymer in an amount of 75 parts polymer solids and 25 parts reaction product solids. The relative cure rates of the respective adhesives, based on a boiling water gel time study were as follows (fastest to slowest cure rate): Ammonia>ethylenediamine>methylamine> ethanolamine>iso-propylamine.

Figure 5:
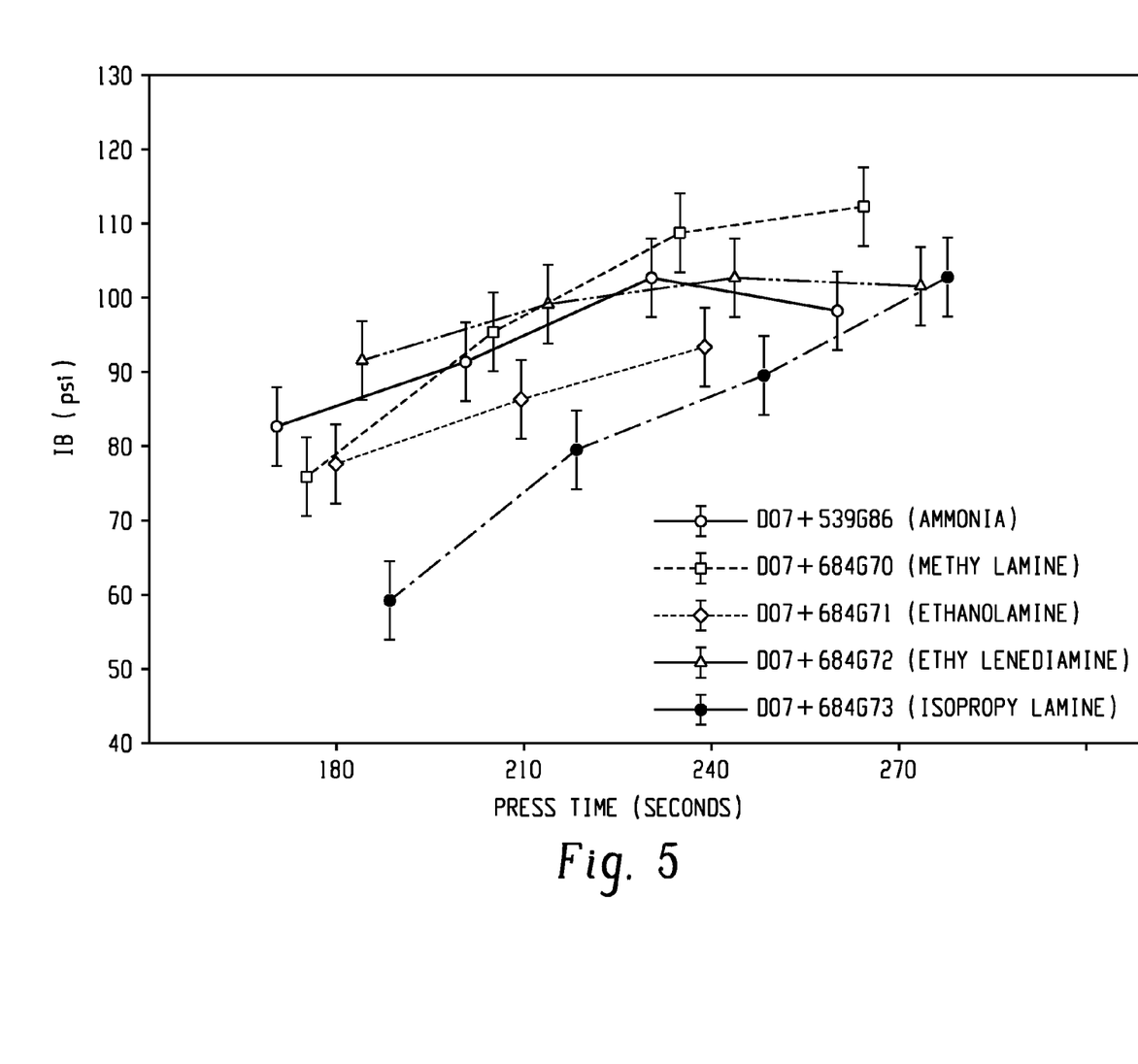
FIG. 5 plots the average internal bond strength (IB) of wood composite panels made at different press times and made using adhesives comprising mixtures of a polyamide bonding component and reaction products of (a) epichlorohydrin and (b) five different amine reactants.

Each of the respective adhesives was used to prepare six (6) ⅝ inch thick panels from the same Southern Yellow Pine wood particles using 6% by weight adhesive solids on the oven dry weight of wood. Four of the panels were prepared at press times between 180 and 270 seconds and were used for IB testing. In addition, two larger boards were prepared using the adhesives made with the epi-ammonia, epi-MA and epi-EDA reaction products (the faster curing adhesives from the boiling water gel time study) at a press time of 240 seconds for MOR and MOE testing. All of the panels were prepared at a target density of 45 pounds per cubic foot (7.2 grams per cubic centimeter). The panels were all pressed at a press temperature of 330° F. (166° C.). The results of the IB testing are presented in FIG. 5. Any differences among the MOR and MOE results for the boards made with the respective adhesives were not statistically significant.

EXAMPLE 5

Synthesis of Epi-Amine Reaction Products at Various Mole Ratios

A series of epi-amine reaction products were prepared in substantially the same way at various mole ratios of epi to ammonia including 2.77:1, 1.75:1, 1.5:1 and 1.25:1. Table 2 presents data on the residual amount of epi, the amount of byproduct 1,3-dichloro-2-propanol and the viscosity of the respective reaction products.

TABLE 2

| Epi/Ammonia Mole Ratio | % Free Epi[1] | % 1,3-dichloro-2-propanol[1] | Viscosity (cps)[2] |
|---|---|---|---|
| 2.77 | 0.099 | 11.5 | 90 |
| 1.75 | ND | 0.53 | 75 |
| 1.50 | ND | 0.34 | 114 |
| 1.25 | ND | 0.22 | 212 |

ND - below a detectable amount

[1]Residual Epi and 1,3-dichloro-2-propanol were determined by Gas Chromotograph/Mass Spectrometry (GC/MS). In subsequent batches of epi-amine reaction product made at an Epi/Ammonia mole ratio of 1.75, a percent free epi value of as high as 0.047% has been detected.
[2]Brookfield viscosity measured at 25° C. using a Digital Viscometer with a small sample adapter (Model DV-II) at 60-100 rpms.

Figure 6:
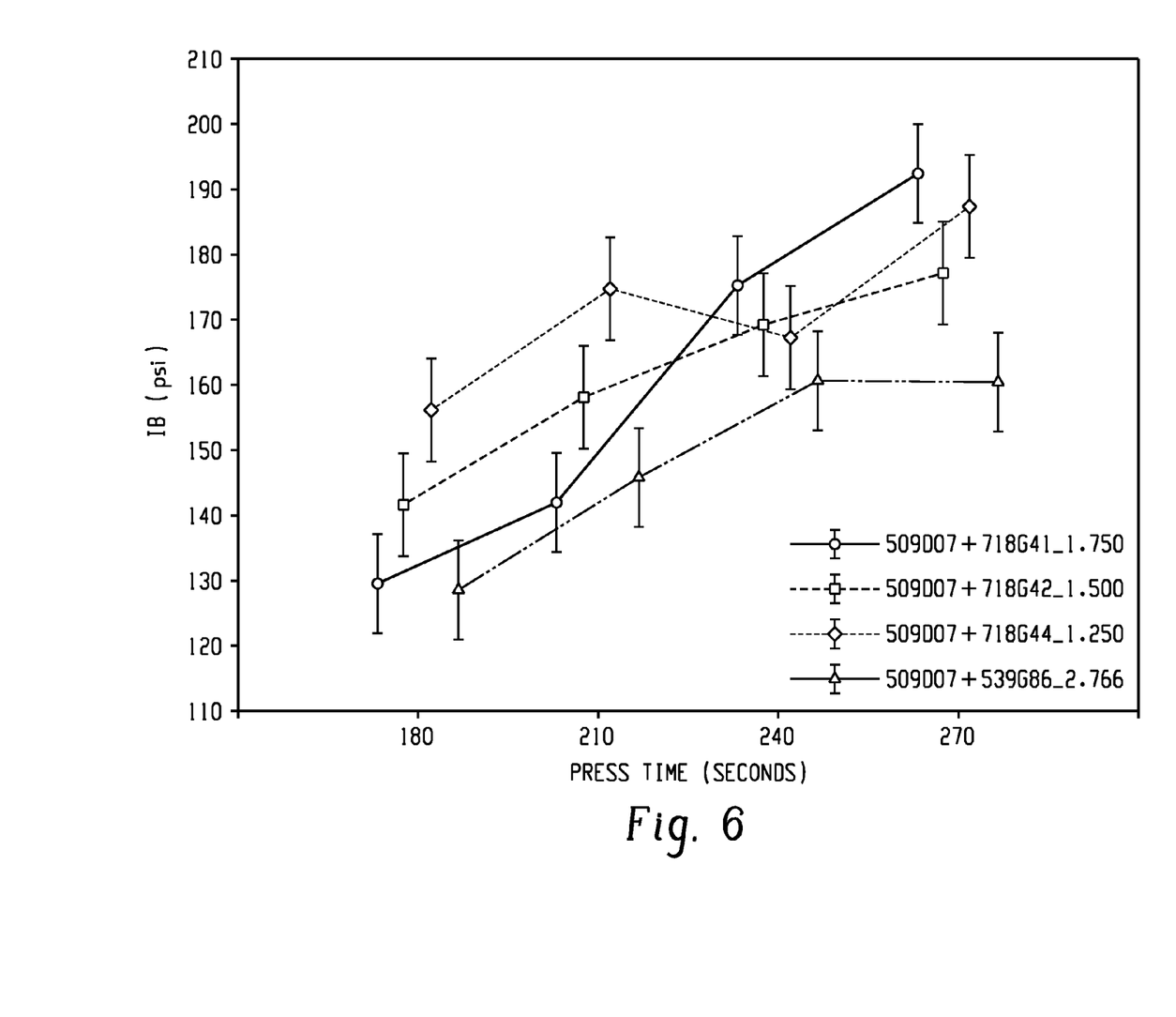
FIG. 6 plots the average internal bond strength (IB) of wood composite panels made at different press times and made using adhesives comprising mixtures of a polyamide bonding component and reaction products of (a) epichlorohydrin and (b) ammonia made at four (4) different mole ratios of epichlorohydrin per atom equivalent of amine hydrogen.

The respective epi-amine reaction products were used to prepare adhesives by blending each of the respective reaction products with the same polyamidoamine polymer in an amount of 66.7 parts polymer solids and 33.3 parts reaction product solids. Each of the respective adhesives was used to prepare six (6) ⅝ inch thick panels from the same Southern Yellow Pine wood particles using 6% by weight adhesive solids on the oven dry weight of wood. Four of the panels prepared at press times between 180 and 270 seconds were used for IB testing, and two of the panels prepared at a press time of 270 seconds were used for MOR and MOE testing, respectfully. All of the panels were prepared at a target density of 48 pounds per cubic foot (7.7 grams per cubic centimeter). The panels were all pressed at a press temperature of 330° F. (166° C.). The results of the IB testing are presented in FIG. 6. For the most part, the differences among the MOR and MOE results for the boards made with the respective adhesives would not be considered statistically significant, except that the board made using the adhesive containing the epi-amine reaction product made at an epi:amine mole ratio of 1.50:1 had a statistically lower MOR than the board made using the adhesive containing the epi-amine reaction product made at an epi:amine mole ratio of 2.77:1.

EXAMPLE 6

Use of Epi-Amine Reaction Product in an MUF Resin

An investigation was conducted to assess the impact of the addition of an epi-amine reaction product on the performance of a low mole ratio MUF resin. The investigation examined the effect of varying the amount of ammonium sulfate catalyst and the amount of epi-amine reaction product on board properties, specifically the IB of the boards. Only one board per press time was tested, which produced a large amount of statistical variation. The strategy of combining an epi-amine reaction product with a low mole ratio resin to produce an adhesive provides an opportunity of improving board properties made using the adhesive without compromising the low formaldehyde emission characteristic of such low mole ratio adhesives. Indeed, as shown in subsequent testing, the epi-amine reaction product itself has the capability of acting as a formaldehyde scavenger, enhancing the low formaldehyde emission characteristics of composites containing the reaction product as an additive.

The epi-amine reaction product was prepared at a mole ratio of epi to ammonia of 2.77:1. The epi-amine reaction product was used to prepare adhesives by blending the reaction product with several low mole ratio MUF formulations to produce five (5) different adhesives. The respective adhesives, Nos. 1 through 5, are summarized in Table 3.

TABLE 3

| Adhesive No. | % MUF on oven dried weight of wood | Epi-Amine as a percentage of Adhesive Solids | Ammonium Sulfate as a percentage of Adhesive Solids |
|---|---|---|---|
| 1 | 8 | 0 | 0 |
| 2 | 8 | 10 | 0 |
| 3 | 8.8 | 0 | 3 |
| 4 | 8 | 0 | 3 |
| 5 | 8 | 10 | 3 |

Figure 7:
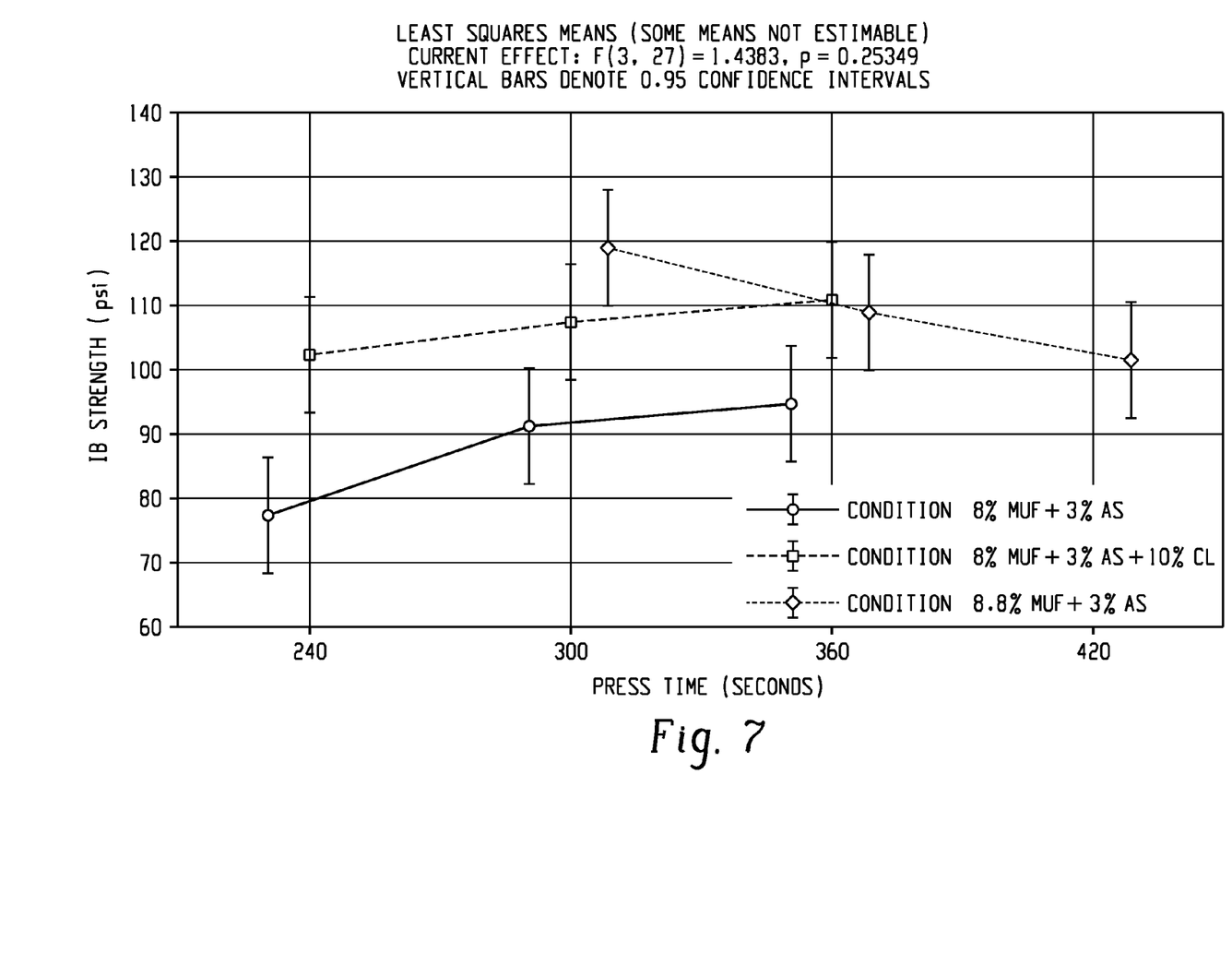
FIG. 7 plots the average internal bond strength (IB) of wood composite panels made at different press times and made using MUF adhesives, one of which has a reaction product of (a) epichlorohydrin and (b) ammonia added.
Figure 8:
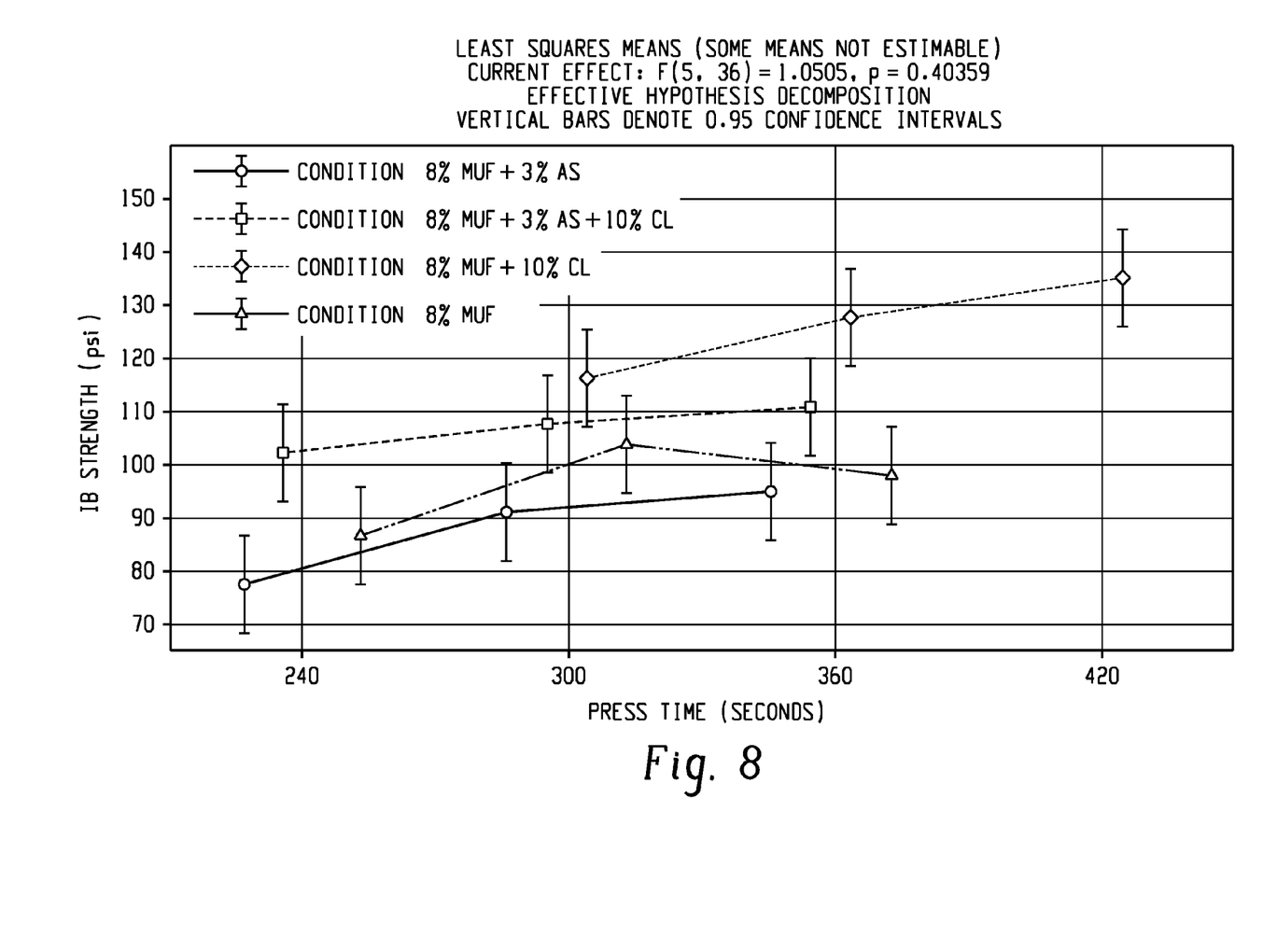
FIG. 8 plots the average internal bond strength (IB) of wood composite panels made at different press times and made using MUF adhesives, two of which have a reaction product of (a) epichlorohydrin and (b) ammonia added.

Each adhesive was used to prepare a single, nominal ⅝ inch thick board at each press time using the same Southern Yellow Pine wood particles and using 8% by weight adhesive solids on the oven dry weight of wood. Boards were prepared at press times between 240 and 420 seconds and were used for IB testing. All of the boards were prepared at a target density of 45 pounds per cubic foot (7.2 grams per cubic centimeter) and at a press temperature of 330° F. (166° C.). The results of the IB testing are presented in FIGS. 7 and 8.

EXAMPLE 7

Comparison of Adhesives for Making Wood Composites

In this example, three different adhesive systems were compared for their ability to produce particleboards from a hardwood and softwood particle furnish[1]: (1) an adhesive of the present invention, combining (a) an epi-amine reaction product made at an epi/ammonia mole ratio of 1.75 (see Example 5) and (b) a commercially available polyamidoamine polymer made with diethylenetriamine and adipic acid (GP 665G11); (2) a commercially available polyamidoamine-epichlorohydrin (PAE-type) adhesive of the type described in US Pub 2007/0054144 (GP 652G03) and (3) a commercially available urea-formaldehyde (UF) adhesive (GP 681G09).

[1] Popular (24%); Pine (36%); OSB (pine flakes)(11%); veneer (popular and pine)(6%); sander dust (Particleboard)(6%); Particleboard saw trim (11%) and Oak (6%)—all percents by weight Each adhesive was used to prepare three boards each having a thickness of 1½ inches. Two of the boards had the dimensions of 18¼ inches by 28¼ inches. One of the boards was 16 inches on each side. Each board was made with 5.5% by weight of the respective adhesive composition. The UF resin also included 1% by weight of a $Al_2(SO_4)_3$ catalyst and 10% by weight urea.

Boards made with adhesives (1) and (2) were pressed for 600 seconds, while the boards made with the UF adhesive were pressed for 570 seconds. The press temperature for making all of the boards was 380° F. (193° C.) and the target density for each of the boards was 30 pcf (0.1 gm/cc).

The boards were tested for Internal Bond strength (IB), Modulus of Rupture (MOR), Modulus of Elasticity (MOE) and formaldehyde emission.

Formaldehyde emissions were measured in a Dynamic Microchamber (DMC), see U.S. Pat. No. 5,286,363 and U.S. Pat. No. 5,395,494, the entireties of which are hereby incorporated by reference. Formaldehyde emissions obtained from this DMC testing are identified as $C_S$. The formaldehyde emission for each adhesive was measured in the DMC using ASTM Method D6007-96 using a single specimen of 7⅞×15" dimensions and the results are presented in the following Table. Internal Bond Strength (IB) was measured using eight (8) 2"×2" specimens, but otherwise in accordance with ASTM: D1037-99 and the average results are presented in the following Table. The Modulus of Rupture (MOR) and Modulus of Elasticity (MOE) were obtained at the same time on each specimen using a total of five (5) specimen strips. The MOR/MOE results were determined on specimens 3"×28¼", but otherwise in accordance with ASTM Method D1037-99 and the average results are presented in the following Table 4.

TABLE 4

| Resin System | IB (psi) | MOR (psi) | MOE (psi) | Formaldehyde (ppm) |
|---|---|---|---|---|
| (1) | 33 ± 2.6 | 717 ± 79 | 556,000 ± 46,000 | 0.025 |
| (2) | 19.3 ± 2.6 | 595 ± 37 | 647,000 ± 48,000 | 0.085 |
| (3) | 7.5 ± 0.8 | 416 ± 26 | 582,000 ± 46,000 | 0.097 |

EXAMPLE 8

Commercial Scale Trial

In this example, the UF adhesive resin system and the adhesive system combining the epi-amine reaction product with a polyamidoamine polymer[2], both as reported in Example 7 above, were compared for their ability to produce particleboard from a hardwood and softwood particle furnish.[3]

[2] The results reported for the present invention in the Table below were obtained following initial pressing efforts aimed at optimizing pre-press conditions. Test results obtained on boards produced during preliminary testing are not reported.

[3] Popular (24%); Pine (36%); OSB (pine flakes)(11%); veneer scrap (popular and pine)(6%); Particleboard sander dust (6%); Particleboard saw trim (11%) and Oak (6%)—all percents by weight Using standard commercial press conditions (platen temperature of 376-384° F. (191-196° C.), 5' by 12' particleboard door cores having a nominal thickness of 1½ inch were pressed to a nominal density of 33 pcf (0.53 gm/cc) using the same adhesive loading reported in Example 7.

The boards were tested for Internal Bond strength (IB), Modulus of Rupture (MOR), Modulus of Elasticity (MOE), and formaldehyde emission.

Formaldehyde emissions were measured in a Dynamic Microchamber (DMC), see U.S. Pat. No. 5,286,363 and U.S. Pat. No. 5,395,494, the entireties of which are hereby incorporated by reference. Formaldehyde emissions obtained from this DMC testing are identified as $C_S$. The formaldehyde emission for each adhesive system was measured in the DMC according to ASTM Method D6007-96 using specimens of 7⅞"×15" dimensions. Specimens were conditioned for 24 hours and 7 days at the 0.04 ft²/ft³ loading ratio for Dore Core prior to testing and the average results are presented in the following Table 5.

Internal Bond Strength (IB) was measured using four (4) specimens in accordance with ASTM: D1037-99 and the average results are presented in the following Table. The Modulus of Rupture (MOR) and Modulus of Elasticity (MOE) values also were obtained using a total of four (4) specimens, in accordance with ASTM Method D1037-99 and the average results are presented in the following Table.

TABLE 5

| Resin System | IB (psi) | MOR (psi) | MOE (psi) | Formaldehyde (24 hr) (ppm)[3] | Formaldehyde (7 day) (ppm)[3] |
|---|---|---|---|---|---|
| (UF) | 40.4 | 469.3 | 113,610 | 0.137 | 0.100 |
| (Invention) | 59.3 | 663.8 | 119,156 | 0.050 | 0.033 |

If what appears to be an anomalous board sample (possibly due to a slug of recycled wood in the furnish that ended up in that board) is excluded from the reported formaldehyde test results for the 24 hr and 7 day emission testing for the inventive adhesive system, then the average values would instead be reported respectively as 0.017 ppm and 0.010 ppm. In either event, a significant reduction in formaldehyde emission is shown by the inventive adhesive system.

The present invention has been described with reference to specific embodiments. However, this application is intended to cover those changes and substitutions that may be made by those skilled in the art without departing from the spirit and the scope of the invention. Unless otherwise specifically indicated, all percentages are by weight. Throughout the specification and in the claims the term "about" is intended to encompass + or −5%.

We claim:

1. A thermosetting adhesive, comprising: a mixture of (1) a bonding component and (2) a reaction product of (a) epichlorohydrin and (b) an amine selected from the group consisting of ammonia, a primary amine, and mixtures thereof, wherein the reaction product is produced by reacting the epichlorohydrin and the amine in a ratio of 0.25 to 0.60 moles of epichlorohydrin per atom equivalent of amine hydrogen.

2. The thermosetting adhesive of claim 1 wherein the reaction product is produced by reacting the epichlorohydrin and the amine in a ratio of 0.25 to 0.40 moles of epichlorohydrin per atom equivalent of amine hydrogen.

3. The thermosetting adhesive of claim 1 wherein the reaction product is produced by reacting the epichlorohydrin and the amine in a ratio of 0.40 to 0.60 moles of epichlorohydrin per atom equivalent of amine hydrogen.

4. The thermosetting adhesive of claim 1 wherein the amine is selected from the group consisting of ammonia, a primary amine and mixtures thereof, wherein the primary amine has a formula $R1-NH_2$ where R1 is a linear alkyl of 1-4 carbon atoms, a linear hydroxy alkyl of 1-4 carbon atoms, or a linear amino alkyl of 1-4 carbon atoms.

5. The thermosetting adhesive of claim 4 wherein the amine is selected from the group consisting of ammonia, methylamine, ethylamine, n-propyl amine, ethanolamine, ethylenediamine and mixtures thereof.

6. The thermosetting adhesive of claim 1 wherein the bonding component is selected from the group consisting of polyamides, phenol-aldehyde condensate resins, amine-aldehyde resins and epoxy resins.

7. The thermosetting adhesive of claim 6 wherein the bonding component is a polyamidoamine polymer.

8. The thermosetting adhesive of claim 6 wherein the bonding component is selected from the group consisting of phenol-formaldehyde (PF) resins, resorcinol-formaldehyde (RF) resins and phenol-resorcinol-formaldehyde (PRF) resins.

9. The thermosetting adhesive of claim 6 wherein the bonding component is selected from the group consisting of urea-formaldehyde (UF) resins, melamine-formaldehyde (MF) resins, melamine-urea-formaldehyde (MUF) resins and phenol-melamine-urea-formaldehyde (PMUF) resins.

10. The thermosetting adhesive of claim 6 wherein the bonding component is selected from the group consisting of a low mole ratio phenol-aldehyde resin and a low mole ratio amine-aldehyde resin.

11. A method for making a composite comprising (A) applying a thermosetting adhesive to a substrate material to form a composite precursor and (B) consolidating the composite precursor under heat to form the composite, wherein the thermosetting adhesive comprises a mixture of (1) a bonding component and (2) a reaction product of (a) epichlorohydrin and (b) an amine selected from the group consisting of ammonia, a primary amine and mixtures thereof, wherein the reaction product is produced by reacting the epichlorohydrin and the amine in a ratio of 0.25 to 0.60 moles of epichlorohydrin per atom equivalent of amine hydrogen.

12. A composite precursor comprising a combination of (A) a substrate material and (B) a thermosetting adhesive, wherein the thermosetting adhesive comprises a mixture of (1) a bonding component and (2) a reaction product of (a) epichlorohydrin and (b) an amine selected from the group consisting of ammonia, a primary amine and mixtures thereof, wherein the reaction product is produced by reacting the epichlorohydrin and the amine in a ratio of 0.25 to 0.60 moles of epichlorohydrin per atom equivalent of amine hydrogen.

13. The composite precursor of claim 12 wherein the reaction product is produced by reacting the epichlorohydrin and the amine in a ratio of 0.40 to 0.60 moles of epichlorohydrin per atom equivalent of amine hydrogen.

14. The composite precursor of claim 12 wherein the amine is selected from the group consisting of ammonia, a primary amine and mixtures thereof, wherein the primary amine has a formula $R1-NH_2$ where R1 is a linear alkyl of 1-4 carbon atoms, a linear hydroxy alkyl of 1-4 carbon atoms, or a linear amino alkyl of 1-4 carbon atoms.

15. The composite precursor of claim 12 wherein the bonding component is selected from the group consisting of polyamides, phenol-aldehyde condensate resins, amine-aldehyde resins and epoxy resins.

16. A composite comprising (A) substrate material bonded into a unitary structure by (B) a cured thermosetting adhesive, wherein the thermosetting adhesive prior to curing comprised a mixture of (1) a bonding component and (2) a reaction product of (a) epichlorohydrin and (b) an amine selected from the group consisting of ammonia, a primary amine and mixtures thereof, wherein the reaction product is produced by reacting the epichlorohydrin and the amine in a ratio of 0.25 to 0.60 moles of epichlorohydrin per atom equivalent of amine hydrogen.

17. The composite of claim 16 wherein the bonding component is selected from the group consisting of phenol-formaldehyde (PF) resins, resorcinol-formaldehyde (RF) resins and phenol-resorcinol-formaldehyde (PRF) resins.

18. The composite of claim 16 wherein the bonding component is selected from the group consisting of urea-formaldehyde (UF) resins, melamine-formaldehyde (MF) resins, melamine-urea-formaldehyde (MUF) resins and phenol-melamine-urea-formaldehyde (PMUF) resins.

19. The thermosetting adhesive of claim 1 wherein the reaction product is spray dried or freeze dried.

20. The thermosetting adhesive of claim 1 wherein a weight ratio of the bonding component solids to reaction product solids is from 95:5 to 60:40.

* * * * *